United States Patent [19]

Foung et al.

[11] Patent Number: 4,777,245
[45] Date of Patent: Oct. 11, 1988

[54] NON-HUMAN PRIMATE MONOCLONAL ANTIBODIES AND METHODS

[75] Inventors: Steven K. H. Foung, San Francisco; Judith A. Blunt, Fremont; Linda B. Rabin, Alameda; F. Carl Grumet, Stanford; Edgar G. Engleman, Atherton, all of Calif.

[73] Assignee: Genelabs Incorporated, Redwood City, Calif.

[21] Appl. No.: 767,213

[22] Filed: Aug. 19, 1985

Related U.S. Application Data

[63] Continuation-in-part of Ser. No. 568,739, Jan. 6, 1984, Pat. No. 4,634,666.

[30] Foreign Application Priority Data

Dec. 31, 1984 [EP] European Pat. Off. ........ 84.309156.2
Jan. 3, 1985 [CA] Canada ..................... 471399
Jan. 7, 1985 [JP] Japan ..................... 60-000268

[51] Int. Cl.$^4$ .......................... C07K 15/00; C12N 5/00; A61K 39/42; A61K 39/44
[52] U.S. Cl. ..................................... 530/387; 435/5; 435/7; 435/68; 435/172.2; 435/172.3; 435/188; 435/240.27; 435/948; 935/96; 424/1.1; 424/86
[58] Field of Search ................ 435/68, 70, 172.2, 240, 435/241, 948, 172.1, 172.3, 5, 7, 188; 424/85, 87, 1.1; 935/89, 90, 95, 96, 99, 100, 102, 106, 108, 109, 110; 436/518, 528–531, 535, 548; 530/387

[56] References Cited

U.S. PATENT DOCUMENTS

4,474,893 10/1984 Reading .................. 436/547
4,529,694 7/1985 Lazarus .................. 435/68

OTHER PUBLICATIONS

Stanley, H. A. et al., Proc. Natl. Acad. Sci., USA, 82: 6272–6275 (9-1985).
Van Meel, F. C. M. et al., J. Immunol. Methods, 80(2): 267–276 (2-1985).
Foung, A. K. H. et al., J. Immunol. Methods 70: 83–90 (5-1984).
Wands, J. R. et al., Proc. Natl. Acad. Sci., USA, 79: 7552–7556 (12-1982).

Primary Examiner—Margaret Moskowitz
Attorney, Agent, or Firm—Ciotti & Murashige, Irell & Manella

[57] ABSTRACT

A stable trioma cell line capable of secreting a non-human primate monoclonal antibody specific against a selected antigen. An exemplary cell line secretes chimpanzee monoclonal antibody specific against an antigen associated with hepatitis nonA/nonB infection. The cell line is produced, in the method of the invention, by isolating lymphocytes from a primate immunized with the selected antigen, and immortalizing the lymphocytes by fusion with a stable, non-antibody-secreting murine myeloma/human hybridoma cell line having selected-for human characteristics. The trioma fusion products are selected for secretion of the desired antibody, which has a variety of diagnostic and/or therapeutic uses.

9 Claims, No Drawings

NON-HUMAN PRIMATE MONOCLONAL ANTIBODIES AND METHODS

The present invention is a continuation-in-part of co-pending U.S. patent application for A Novel Fusion Partner and Its Products, Ser. No. 568,739, filed 6 Jan. 1984 now U.S. Pat. No. 4,634,666 issued Jan. 6, 1987.

1. FIELD OF THE INVENTION

The present invention relates to non-human primate monoclonal antibodies, to stable trioma cell lines capable of secreting such antibodies, and to a method for forming the trioma lines.

2. REFERENCES

The following references are referred to herein by corresponding number:
1. Alter, H., et al, *Lancet*, 1: 459 (1978).
2. Kozbor, D., et al., *Hybridoma*, 1: 323 (1982).
3. Olsson, L., et al, *Proc Nat Acad Sci* (USA), 212: 767 (1980).
4. Nowinski, R., et al, *Science*, 210: 537 (1980).
5. Lane, H. C., et al, *J Exp Med*, 155: 333 (1982).
6. Foung, S. K. H., et al, *J Immunol Meth*, 70: 83 (1984).
7. Clark, E. A., et al, *Immunogenetics*, 18: 599 (1983).
8. Sly, W. S. et al, *Tissue Antigens*, 7: 165 (1976).
9. Kohler, G., et al, *Nature*, 256: 495 (1975).
10. Grumet, F. C., et al, *Human Immunol*, 5: 61 (1982).
11. Boyum A., *Scand J Lab Clin Invest*, 21: (Supp. 97)77.
12. Shimizu, P., et al, *Nat Acad Sci*, 82: 2138 (1985).

3. BACKGROUND OF THE INVENTION

Monoclonal antibodies (Mabs) have been widely used in diagnostics, and there is a growing interest in their use in human therapy. Although the original and still most successful procedure for generating Mabs is by way of mouse-cell hybridomas, mouse Mabs have a number of limitations, both in diagnostic and therapeutic uses.

In the diagnostics area, it would be extremely valuable, in diagnosing propensity to disease and for purposes of transplantation or transfusion matching, to be able to recognize many of the polymorphisms in human cell surface alloantigens, e.g., histocompatibility antigens. Efforts to obtain mouse Mabs which are specific against individual polymorphisms, such as red blood cell alloantigens and histocompatibility antigens have had only very limited success, because the immunized mice appear to preferentially react immunologically to species-specific "backbone" determinants that are shared by all such antigens, rather than to the polymorphic determinants that vary among individuals of a population. Ideally, one would like to produce the polymorphic-specific Mabs in a non-human primate, such as the chimpanzee, which is phylogenetically close to humans, and which would therefore be expected to share many of the same antigenic backbone determinants with humans.

In some human diseases for which Mab-based diagnosis would be valuable, such as hepatitis nonA/nonB (NANB), the infective agent(s) has not been identified and, therefore, mouse B lymphocytes specific against the agent have not yet been obtained. In this example, the only known biological assay of NANB infectivity is transmission to chimpanzees (reference 1). For this reason and with this particular agent, as well as others for which antigen-specific human B lymphocytes also have not yet been obtained, it would be desirable to be able to produce Mabs using sensitized B lymphocytes obtained from infected non-human primates.

In the therapeutics area, mouse Mabs are expected to be of limited value, especially where multiple injections of the antibody must be given, because of the likelihood that the patient will develop a severe immunological response to the foreign antibodies. Although the immune response problem may be solved by use of human Mabs, there are also significant limitations associated with deriving humabn Mabs against many selected antigens. One of the limitations which has been encountered in producing human Mabs is in immortalizing human B lymphocytes in a manner that leads to stable antibody-producing cell lines. Heretofore, two major approaches for producing human Mab-secreting cells have been used: direct immortalization of immunized lymphocytes with Epstein-Barr Virus (EBV) and Mab production by hybridomas formed between immortalized human B cell lines (EBV), lymphoblastoid, or human or murine myelomas, and human B lymphocytes from an immunized host. Neither of these approaches has proved entirely satisfactory.

It is common experience among practitioners in the art that EBV transformation, while successful in forming Mab-secreting cultures, will often fail to provide antigen-specific EBV transformed cells which have sufficiently long life spans to provide reliable sources of the desired antibodies (reference 2). Thus, this method fails to provide reliably for antibody production over extended periods. Previously produced hybridomas between immunized human B cells and appropriately drug marked mouse or human myeloma or human lymphoblastoid cell lines have suffered from low frequency of hybrid formation in the case of human-human hybridizations (reference 3) or chromosomal instability in the case of murine-human hybridomas (references 4 and 5).

The problem of producing a stable, human Mab-producing cell line has been addressed by the inventors in the above co-pending application of A Novel Fusion Partner and Products. Briefly, it was discovered that stable, human Mab-secreting cell lines could be produced by (a) constructing a mouse myeloma/human lymphocyte hybridoma cell line having certain selected-for characteristics, and (b) fusing the hybridoma with a human B lymphocyte from an individual immunized with a selected antigen. The method disclosed in the above co-pending application is described generally in reference 6. Relevant aspects of the trioma-cell invention will be given below.

Although the above trioma method can be used to generate stable, human Mab-secreting cells, it is limited, as are the other human Mab methods mentioned above, to antibodies for which active B lymphocytes are available from human donors. In many cases, it is either not possible to immunize humans, e.g., where toxins, active viruses, or the like are involved, or it is difficult to identify individuals that have been recently immunized to the antigen of interest.

An alternative source of B lymphocytes for use in producing Mabs suitable for human therapy are non-human primates. Mabs from primates, such as the chimpanzee, which are phylogenetically similar to humans would be much less likely to cause an anti-immunoglobulin response to humans that would Mabs from a source such as mice. At the same time, the animals could be immunized with a variety of antigens which cannot be administered to humans, and the antigen-specific B lymphocytes could be obtained at an optimal time after immunization. For the agent(s) responsible for NANB hepatitis, chimpanzees are the only experimental animals known to be susceptible to this disease.

4. SUMMARY OF THE INVENTION

It is therefore a general object of the invention to provide stable cell lines that secrete non-human primate Mabs, and a method for producing such lines.

A related object of the invention is to provide non-human primate Mabs for use in diagnostic applications, where murine or human Mabs are unavailable, and for human therapeutic uses, where human Mabs are not readily obtainable.

One specific object of the invention is to provide a stable cell line which secretes a chimpanzee Mab specific against NANB antigen, and a method of generating such antibodies.

The invention includes a stable cell line capable of secreting non-human, primate Mab specific against a selected antigen. In one embodiment of the invention, the cell line secretes chimpanzee Mabs, and in a specific case, chimpanzee Mabs which are reactive against an antigen present in liver infected with a nonA/nonB (NANB) hepatitis viral agent.

The stable cell line is produced, according to one aspect of the invention, by obtaining B lymphocytes from a sensitized or immunized non-human primate and fusing them with the murine myeloma/human hybridoma fusion partner described in the above co-pending patent application for A Novel Fusion Partner and Its Products. The fusion partner is prepared, as disclosed in the above-cited co-pending application, by fusing mouse myeloma cells with human B lymphocytes. The fusion product is selected for stable immunoglobulin secretion and HLA surface antigen expression. The selected fusion product is then mutagenized and further selected for non-secretion of immunoglobulins, but retention of HLA antigen expression.

Fusion of non-human primate B lymphocytes with the immortalizing hybridoma produces the desired stable cell line capable of secreting a non-human primate Mab specific against a selected antigen. The cell line is a mouse myeloma/human lymphocyte/non-human primate lymphocyte fusion product which is designated a "primate trioma". This term is used to distinguish the stable, primate Mab-secreting cell lines of the present application from the "triomas" disclosed in the above co-pending application, which result from the fusion of the murine myeloma/human fusion partner with human B lymphocytes. A specific embodiment of a primate trioma formed in accordance with the invention secretes chimpanzee Mab specific against NANB. This trioma has been designated GLH-01, deposited at the ATCC on or about 15 Aug. 1985, and assigned the ATCC number HB 8884.

These and other objects and features of the invention will become more fully apparent from the following detailed description of the invention.

DETAILED DESCRIPTION OF THE INVENTION

I. Definitions

As used herein, "trioma" refers to a cell line which contains genetic components originating in three originally separate cell lineages. As used in the context of this application, these triomas are stable, immortalized antibody producers which result from the fusion of a murine myeloma/human hybridoma with a non-human, primate antibody-producing B cell.

The murine myeloma/human hybridoma (the "immortalizing hybridoma") is an immortal cell line which results from the fusion of a murine myeloma or other murine tumor cell with human lymphoid cells derived from a normal (preferably non-immunized) subject. As described below, by careful selection and mutation, an immortalizing hybridoma which provides improved chromosomal stability, has human characteristics, and which does not secrete immunoglobulin is obtained. The antibody secreting capacity of the trioma is provided by the third member of the fusion which is typically derived either from B cells of an immunized non-human primate, or with such B cells altered so that they, too, are immortal.

"Non-secreting" hybridoma refers to a hybridoma which is capable of continuous reproduction and, therefore, is immortal, which lacks the capacity to secrete immunoglobulin.

A hybridoma "having human characteristics" refers to a hybridoma which retains detectable human-derived chromosomes, such as those producing human HLA antigen which will be expressed on the cell surface.

Lymphoid cells "immunized against a predefined determinant" refers to lymph cells derived from a non-human primate which has been exposed to an antigen having the determinant of choice. Thus, for example, a primate can be induced to produce from its lymphoid B cells, antibodies against antigenic determinants of specific viruses or bacteria, by virtue of exposure through past infections or vaccinations. B cells which produce such antibodies are defined by this term.

"Cell line" refers to various embodiments including but not limited to individual cells, harvested cells, and cultures containing cells so long as these are derived from cells of the cell line referred to. By "derived" is meant progeny or issue. It is further known in the art that spontaneous or induced changes can take place in karyotype during storage or transfer. Therefore, cells derived from the cell line referred to may not be precisely identical to the ancestral cells or cultures, and an cell line referred to includes such variants.

II. Preparing Non-Human Primate Mabs

A. Component Cell Lines

The cells which make up the immortalizing hybridoma are murine myeloma cells and human lymphoid B cells. Murine myeloma cell lines are commonly available and may be obtained through the American Type Culture Collection (ATCC), located at the National Institutes of Health (NIH) in Bethesda, Md. Human lymphoid B cells are isolated from the plasma of normal individuals using conventional techniques. Such procedures include density gradient purification and separation of B cells from T cells using standard sheep erythrocyte rosetting techniques known in the art.

The primate B lymphocyte, antibody-producing component of the trioma can be prepared using standard techniques. The selection of a primate source will depend on a variety of factors, including availability of animals, infectivity, and immune response with respect to a given infective agent, and phylogenetic similarity to man. Chimpanzees are generally preferred, particularly where the primate Mabs are intended for human therapeutic use because of their phlogenetical similarity to humans, and are required where, as in the case of NANB described below, infectivity is limited to chimpanzees. Other hominids, such as gibbons, gorillas, and orangutans, show close similarities to humans in immunological genes (reference 7), and are also generally suitable for use in the invention.

Where the desired primate Mab is directed against a determinant associated with a viral or bacterial infective agent, antigen-specific lymphocytes may be derived from an animal identified as having been infected with the agent, or from an animal infected by deliberate inoculation. The B lymphocytes are preferably isolated from a blood sample taken at or near the peak of the immune response, i.e., at the point of highest antigen-specific antibody titer. Typically, this peak is between about one and three weeks, and usually about two weeks after immunization. One suitable method for isolating peripheral blood lymphocytes from blood samples is given in reference 6.

The isolated B lymphocytes can be used without further treatment for fusion with the immortalizing hybridoma. Alternatively, the lymphocytes can themselves be immortalized, for example, by in vivo transformation, before being fused with the immortalizing hybridoma. In one transformation method, the lymphocytes are infected with Epstein-Barr Virus (EBV) and transformants are selected for their ability to grow in culture. A standard EBV-transformation procedure is described in reference 8. The EBV-transformed cells may be enriched for secretion of an antibody having a desired antigen specificity, by conventional antibody screening methods, such as those described below in Section IIF. Procedures for producing EBV-transformed B lymphocytes from chimpanzees immunized with NANB, and for enriching cells which secrete an antibody reactive against liver tissue infected with NANB hepatitis agent are given in Example II. In another procedure, the cells may be activated by long-term exposure to a mitogen, such as pokeweed mitogen, in culture (reference 6).

Transformed or mitogen-activated B lymphocytes can give more efficient production of triomas, due to the greater number of lymphocytes available for fusion with the immortalizing hybridoma. As noted above, cells transformed or activated in this manner are, by themselves, unstable antibody producers in culture, and are therefore generally unsuitable for long-term antibody production.

B. Fusion Procedures

Fusions to form the murine-human non-secreting hybridomas and the triomas of the inventions are performed by a modification of the method of Kohler and Milstein (reference 9). Briefly, a tumor cell line (to make the immortalizing hybridoma) or hybridoma (to make the triomas) is combined with the partner cells (typically spleen cells or B lymphocytes) that produce the antibody of interest, using a fusogen such as polyethylene glycol under suitable conditions, e.g., 40%–50% polyethylene glycol (1000 to 4000 molecular weight) at between room temperature and 40° C., preferably about 37° C. Fusion requires about 5–10 minutes, and the cells are then centrifuged and screened.

C. Screening Procedures

Following the fusion procedure, screening for hybridized products is made by culturing cells centrifuged from the fusion medium in growth medium which is selective for the desired hybrids. Ordinarily, non-immortalized cells cannot survive repeated transfers on any medium, and hence will not survive repeated culturing of the centrifuged cells. Commonly used lines of immortalized murine myeloma cells, however, are incapable of growth on certain selective media which have been chosen to deprive them of their ability to synthesize DNA. Two very commonly used media of this description are "hypoxanthine-aminopterin-thymidine" or "HAT" medium and azaserine-hypoxanthine medium or "AH" medium.

Both of these selection media take advantage of the capacity of normal cells to utilize a "salvage" pathway for DNA synthesis under circumstances where the de novo process is inhibitied. Aminopterin inhibits both purine and pyrimidine nucleotide do novo synthesis in normal cells and both thymidine and hypoxanthine are required for the salvage pathway. Azaserine inhibits only purine synthesis, so only hypoxanthine is required for the salvage pathway.

The salvage process, which requires hypoxanthine phosphoribosyl transferase (HPRT) is generally inoperable in the commonly used murine myeloma cells (although they retain the de novo pathway). Since aminopterin (in the HAT medium) or azaserine (in the AH medium) are both inhibitors of the de novo DNA synthesis pathway, the murine myeloma cells are incapable of growth in either "HAT" or "AH" medium. Thus, only hybridized cells can both survive repeated transfers and grow in HAT or AH medium. Normal lymphocytes cannot survive because they are not immortalized, and do not survive repeated transfers; unhybridized tumor cells cannot survive because they lack the salvage pathway which permits the use of hypoxanthine to overcome aminopterin or azaserine inhibition.

In those special instances where the immortalized hybridoma is to be fused to a transformed antibody-producing cell, e.g., an EBV-transformed B lymphocyte, an additional property is required. The transformed antibody producer does not die from multiple transfers as would a normal cell and, unlike the common murine myeloma immortalizing lines, is not sensitive to HAT or AH medium. Thus, the usual selection means will permit unfused, transformed lymphocytes to survive. A screening procedure for successful triomas thus requires inclusion in the medium of a drug, such as ouabain, to which the EBV-transformed B cells are sensitive. Therefore, the immortalizing hybridoma must, in addition to other desired properties, have acquired resistance to this drug so that it can transfer resistance to the trioma.

D. The Immortalizing Hybridoma

The selection procedures employed in producing the immortalizing hybridoma are aimed at selecting cells which show stable human characteristics, non-secretion of immunoglobulin, sensitivity to a medium to which the fusion partner will be resistant, and, if an immortalized primate lymphoid partner is used, resistance to a drug capable of destroying the lymphoid partner. This particular collection of characteristics requires a unique and well-designed screening and mutagenesis process.

Briefly, the cells centrifuged from the fusion mixture of mouse myeloma and human lymphoid cells are diluted and plated in microtiter plates. Screening is done using AH or HAT medium growth, with selection of successful colonies being made on the basis of assay procedures related to stability and human character. From among the many colonies assayed, several are chosen which continue to produce immunoglobulin in the supernatant fluid for a suitable period of time, preferably in excess of six months (one criterion for stability). The continued production of such immunoglobulin indicates that the characteristics conferred by the human lymphocyte partner have not been lost (lymphocytes which were unfused will, of course, not survive). Retention of human characteristics is assessed by assaying the cell surfaces for the presence of HLA antigen. The selected colonies continue to exhibit HLA antigen expression at their cell surfaces (another indication of stability, as well as human character).

The selected clones are then subjected to a mutagen, such as 6-thioguanine, to destroy their ability to secrete immunoglobulin and confer HAT or AH sensitivity, and, where appropriate, resistance to a drug such as ouabain. This will make possible later fusion to give a primate trioma, and subsequent use of the fusion product to secrete only the particular primate Mab characteristic of the primate lymphoid partner. According to an important feature of the cell selection medium, the mutagenized cells are further selected for retention of HLA antigen expression on the cell surface.

Example I below describes the preparation of an immortalizing hybridoma which is generally useful in producing primate triomas according to the invention. The cell line, designated SBC-H20, has the selected characteristics noted in the example. The cell line was deposited with the American Type Culture Collection (ATCC), 12301 Parklawn Drive, Rockville, Md. 20852 on or about 13 Dec. 1983 and given the designation ATCC HB 8464.

E. Primate Triomas

The immortalizing hybridoma and primate B lymphocytes from above are fused under conditions like those outlined in Section IIB. Typically, the primate cells are mixed with the immortalizing hybridoma cells at a ratio of between about 1:1 to 1:2. The primate lymphocytes used are preferably first transformed or activated in vivo according to above procedures, although untransformed cells have also been used successfully. The cell mixture is freed of serum by washing, and resuspended in polyethylene glycol to promote cell fusion. After a suitable incubation period, the cells are washed, resuspended in culture medium, and plated on microtiter wells. Example III below illustrates the preparation of a primate trioma for production of chimpanzee anti-NANB Mabs.

The resulting fusion products are selected using an appropriate selection medium. If the antibody-producing partner is a normal cell line, selection medium can simply be the HAT or AH medium which will discriminate against unfused immortalizing hybridoma cells—the antibody producer fails to maintain immortality in successive transfers. If the antibody producer is itself an immortalized cell—i.e., for example, a virus transformed lymphocyte—an additional selection in the presence of, for example, ouabain to prevent growth of the unhybridized cells is also required.

Fusion products are screened initially for ability to produce primate immunoglobulin, preferably using conventional solid-phase immunoassay methods for detecting immunoglobulin in the cell culture supernatant. It is noted that since the immortalizing hybridoma is itself incapable of secreting immunoglobulins, only successful fusion products will be detected.

In the usual solid-phase assay method, a solid surface coated with anti-immunoglobulin antibodies is reacted with the cell culture supernatant, binding supernatant immunoglobulins to the support surface. The surface-coated antibodies are preferably specific against a selected class (e.g., IgM or IgG) or IgG subclass of primate antibodies, to permit selection and/or identification of fusion products which produce a selected antibody type. Because of the close structural relationship between human and primate (particularly chimpanzee) antibodies, class-specific anti-human immunoglobulin antibodies may be employed. Purified goat antibodies against human immunoglobulins of specific classes and subclasses are commercially available, for example, from Zymed (San Francisco, CA).

The presence of primate immunoglobulins bound to the solid support is detected by anti-primate immunoglobulin antibodies which are labeled with a detectable reporter, such as a fluorophore, chromophore, enzyme, or radioisotope label. The labeled antibody is preferably one which is specific against the Fab portion of the primate antibody, and, in any case, must be able to bind to the primate antibody, with such bound to the solid support. The presence of primate antibody in trioma supernatant is confirmed by the presence of label on the washed support. Example III below illustrates an enzyme-linked immunoassay (ELISA) for detecting primate IgM and IgG antibody secretion in the trioma cell lines from the example. F. Primate Mabs Successful fusion products are further screened for the presence of primate Mabs which are specific against a selected antigen. The choice of methods used for detecting the desired Mab will depend on the nature of the antigen and/or labeled antibody reagents which are available. Where the primate Mab is to be selected for specificity against a cell-surface antigen, the desired Mab can be detected by contacting cell-culture supernatant with cells carrying the antigen. The presence of bound primate antibodies on the cells is then detected using a labeled anti-primate immunoglobulin antibody, as described in Section IIE.

For identifying Mabs which are specific against isolated antigenic material, the antigen may be coupled to a solid support, which is contacted with cell supernatant, to bind the desired Mab. Labeled anti-immunoglobulin is used, as above, to detect primate Mab bound to support.

The antigen of interest may be associated with and/or bound to biological tissue. Such is the case, for example, with some infectious agents, such as NANB, which are thought to invade a particular organ. Here the infected tissue, obtained, for example, in biopsied form, will provide a suitable "substrate" to which antigen-specific Mabs can bind, the bound primate Mabs then being detected by labeled anti-immunoglobulin antibodies. Example IV describes the selection of chimpanzee Mabs reactive against liver tissue obtained from chimps infected with NANB hepatitis infective agent, but not reactive against normal (uninfected) chimp or human liver tissue.

Triomas that produce non-human primate antibodies having the desired specificity may be subcloned by limiting dilution techniques and grown in vitro in culture medium or injected into selected host animals and grown in vivo.

III. Uses of Primate Mabs

A. Purifying Antigens

As indicated above, there are two important classes of antigens for which non-human primate Mabs are uniquely suited: (1) antigens associated with a human infectious agent, such as NANB, which is infective in primates but not mice, and (2) polymorphic human histocompatibility antigens. Due to the limited availability of either human or murine Mabs against antigens in these classes, non-human primate Mabs provide a convenient, and in some cases the only available method for obtaining these antigens in purified form.

As a first step in antigen purification, an antigen-specific primate Mab, prepared according to the above methods, is coupled to a solid support to make an effective adsorbent reagent for affinity purification of the selected antigen. Reactions for coupling Mabs to a variety of solid support materials, such as polymer or glass beads, are well known. The affinity support material may be used in either batch or column purification, according to standard methods. Typically, a solution of the antigen in cold buffer, pH 7–8, is passed through a column of the support material, which is then washed extensively to remove unbound contaminants. The retained antigen is eluted from the support by a suitable eluant.

To illustrate, the primate anti-NANB Mab from Example IV is coupled to polymer beads, and used to isolate NANB antigen material present in the serum of a NANB-infected human or chimpanzee source.

The isolated antigen or antigen material may be attached to a solid support, for use in an immunoassay for detecting antibodies against the antigen. In another application relating to isolated pathogenic material, the antigen (or isolated pathogen) can be used to identify nucleic-acid and/or peptide sequences associated with the pathogen or disease-associated antigens induced in infected hosts, for purposes of generating large amounts of these antigens or parts of antigens for use in diagnostic immunoassays or for constructing a vaccine against the virus.

B. Diagnostic Uses

As indicated above, it would be highly desirable, for purposes of diagnosing disease and transplantation or transfusion matching, to be able to identify allo-specific cell surface antigens, e.g., those associated with human histocompatibility genes. This can be done, according to one aspect of the invention, by first preparing a bank of non-human primate Mabs against individual-specific (polymorphic) cell surface antigens. In the case of disease diagnosis, the selected antigens are those whose polymorphisms are known to correlate with diseases of interest.

The primate Mabs obtained may be used to detect individual-specific cell surface antigens by a number of known methods. In one widely used method, the primate Mabs are reacted with antigen-bearing leukocytes in the presence of serum complement (reference 10). The presence of the antigen of interest is indicated by leukocyte microcytoxicity, resulting from complement damage at the site of antigen/antibody interactions on the cell surface. In another method, the primate Mabs are labeled with a suitable reporter, such as an enzyme, fluorophore, or radioisotopic label, and the labeled Mabs are reacted with cells carrying the surface antigens of interest. Binding of Mabs to the cells is determined by measuring the extent of reporter associated with the cells. A similar type of assay can be carried out with unlabeled Mabs, by first binding the Mabs to the cells, then reacting the cells with a labeled anti-immunoglobulin antibody specific against the unlabeled Mabs. Finally, hemagglutination methods involding direct cell agglutination by the Mabs or indirect agglutination in combination with a Coombs reagent are generally useful for identifying transplantation antigens.

Another important diagnostic use of primate Mabs is for detection of human infectious agents, such as NANB, for which human or mouse Mabs are difficult or impossible to obtain. The nature of the test will depend on whether the infection is more easily detected by the presence of serum antigens, or anti-antigen antibodies induced in the infected individual. In the former case, the assay system is preferably a sandwich-type solid-phase assay system based on immunospecific binding of the infectious-agent antigen (or host antigens induced by the infectious agent) to primate Mabs attached to a solid support, and subsequent binding of labeled anti-antigen antibody to the support-bound antigen. The Mabs attached to the support may be specific against the same or a different antigen epitope as the labeled antibody.

Assays for detecting infection-induced antibodies may also use a sandwich-type, solid-support system. Here, however, it is the induced human antibody, rather than the infectious antigenic material, that functions to bind a labeled (anti-immunoglobulin) antibody to the support. The assay system is constructed by attaching the purified antigen of interest, e.g., NANB antigenic material, to a solid support. The antigen is preferably one whose isolation and purification is made possible by combining the primate Mab methods of the invention with the affinity binding approach described in Section IIIA. Since a number of purified antigens not heretofore available can be obtained in this manner, the present invention for producing primate Mabs effectively expands the range of analyte antibodies that can now be assayed. In particular, solid-support immunoassay systems for the detection of antibodies induced against certain pathogenic agents, such as NANB, are readily prepared.

As a first step in the assay, the analyte serum is reacted with the solid support having the surface-bound antigen. The support is then contacted with labeled anti-immunoglobulin antibodies, to bind the label in proportion to the amount of analyte antibody bound to the support. After washing the support, the amount of bound label is determined by conventional methods. It is noted that non-human primate Mabs may be used to "capture" or immobilize serum antigen to a solid support (sandwich assay) or, alternatively, may not themselves serve as a reaction component of the assay, but be used instead for purifying the support-bound antigen.

Another variation on this technology would employ the use of anti-idiotype antibodies to detect anti-NANB antibody in patients. Specifically, the primate monoclonal anti-NANB antibodies can be used as immunogens in mice to produce murine anti-primate (NANB) idiotype antibodies. These murine reagents then could be used to detect human anti-NANB antibodies whose idiotypes cross-react with the relevant primate idiotypes. Methods of detection would be analogous to those just described for detecting anti-NANB antibodies by use of purified NANB antigen, substituting the anti-idiotype antibody for the NANB antigen.

III. Therapeutic Uses

The therapeutic uses of the present invention derive from the ability to produce Mabs which are antigenically similar to human Mabs, but which can be prepared against a variety of antigens, such as infective agents, toxins, and the like, for which human Mabs are unavailable.

The desired Mabs are prepared as above, where the B lymphocytes used are isolated from an animal which has been immunized with the antigen, e.g., infectious agent or toxin, of interest. The Mabs are preferably prepared using B lyphocytes from chimps or other humanoids, to minimize human immune response to the foreign antibodies. The Mabs obtained from the trioma supernatant are purified, by conventional methods. The method for producing chimpanzee anti-NANB Mabs described in Example IV is illustrative.

From the foregoing, it can be appreciated how various objects and features of the invention are met. The invention provides for the production of non-human primate Mabs by stable cell lines, i.e., cell lines whose growth and antibody-secreting levels are substantially invariant from generation to generation. This insures high levels of antibody production over time, and reduces problems of quality control which arise when unstable antibody-secreting cell lines are used.

The method of the invention can be used to generate primate Mabs specific against a variety of antigens for which human or murine Mabs are not available. These include immune-response antigens and the antigens of human infectious agents which do not infect mice. Mabs against these antigens are useful for (a) isolating and purifying antigens which cannot otherwise be obtained, (b) identifying immune-response gene polymorphisms in humans, (c) detecting human infectious agents, such as NANB, which cannot now be detected by practical methods, and/or (d) antibody treatment in humans where human Mabs are not available.

EXAMPLES

The following examples illustrate various aspects of the invention, but are in no way intended to limit the scope thereof.

EXAMPLE I

Preparation of Immortalizing Hybridoma SBC-H20

Mouse myeloma cell line SP20/08A2 was obtained for use as the immortalizing partner from Frank Fitch, University of Chicago. This cell line is freely available and can be used without restriction. Other mouse myeloma lines are also readily available. Human preipheral B lymphocytes were isolated from the heparinized plasma of a normal human donor by Ficoll-Hypaque gradient as described in referece 11. The peripheral B lymphocytes B and myeloma cells were mixed at a 1:1 ratio, washed once in RPMI 1640 medium (Gibco), and pelleted at 250×g for 10 min. The pellet was gently resuspended in 1 ml of RPMI with 40-45% (V/V) polyethylene glycol solution, MW 1430-1570 (BDH Chemicals, Poole, England) which was pre-warmed to 37° C. After two min at room temperature, the cell suspension was diluted to 6 ml with RPMI, centrifuged at 500×g for 3 min, and, beginning 8 min from the onset of fusion, the cell pellet was washed with RPMI containing 10% fetal calf serum (FCS). The pelleted cells were plated in multi-well trays using suitable dilutions to obtain individual clones. The colonies were grown on AH selection medium containing 2 µg/ml azaserine and 100 µM hypoxanthine, and successful clones were assayed for immunoglobulin production and for HLA surface proteins using the assay methods described in reference 6.

A hybrid clone which had had a stable immunoglobulin production for 6 months, and which was consistently producing HLA surface protein, was selected.

This clone was placed in Iscove's medium (IDMEM) (Gibco) containing 10% FCS, 2 mM glutamine, 100 unites penicillin, 100 mg streptomycin per ml, as well as the mutagen 6-thioguanine (Sigma, St. Louis, MO). The concentration of 6-thioguanine was progressively increased to $2\times10^{-5}M$ ouabain over a period of approximately 30 days. The resultant mutant hybrids were sub-cloned, and the colonies tested for immunoglobulin secretion. A non-secreting sub-clone which was HAT-/AH sensitive, resistant to $10^6$ ouabain, and which retained the ability to produce HLA surface antigen was selected. A sample of this cell line which is designated SBC-H20 was deposited with the ATCC and has the deposit identifying no. ATCC HB 8464. The characteristics of this murine-human hybridoma include: sensitivity to HAT and AH media, resistance to ouabain (Sigma) to a concentration of $10^{-6}M$, non-secretion of immunoglobulins, human chromosomal stability over time, and production of HLA surface protein.

EXAMPLE II

Preparation of EBV-Transformed Anti-NANB

Lymphocytes were isolated by density-gradient centrifugation of peripheral blood taken from a chimpanzee recently infected with and presumably sensitized to NANB hepatitis. T cells were removed by a conventional single-step sheep erythrocyte rosetting method, using 2-aminoethyl-isothiouronium bromide hydrobromide. The remaining B cells were transformed by the EBV-containing supernatant of the marmoset line B-958 for 2 hr at 37° C. The cells from the transformed mixture were transferred to microtiter plates at a concentration of $10^4$ and $10^3$ cells per well, and cultured for 21 days in IDMEM with 20% fetal calf serum FCS. The cell supernatants were assayed for NANB-specific antibodies by indirect immunofluorescence on sections of NANB-infected liver tissue, according to a modification of the method of reference 12. Positive wells were expanded for future fusion.

EXAMPLE III

Preparation of Chimpanzee Triomas Secreting IgG and IgM Antibodies

Lymphocytes were isolated and T cells removed from a blood specimen taken from an NANB-infected chimpanzee, as in Example II. The isolated cells were mixed with the hybridoma cell line SBC-H20 (Example I). at a cell ratio of about 1:2. The cells were washed in IDMEM without serum and pelleted. The pellet was gently resuspended in 1 ml of IDMEM with 45% (v/v) polyethylene glycol solution, MW 1430-1570 (BDH Chemicals, Poole, England) which was prewarmed to 37° C. After 2 min at room temperature the cell suspension was diluted to 6 ml with IDMEM, centrifuged at 500 g for 3 min, and beginning at 8 min from onset of fusion, the cell pellet was washed with 10% FCS. The pelleted cells were diluted to give $10^5$ to $10^4$ cells per well.

Alternatively, EBV-transformed cell lines were derived from the sensitized chimpanzee B cells, and enriched by successive passage in microtiter wells for 3 weeks before fusion.

IgG and IgM secretion by the fusion products in the cell supernatants was determined by enzyme-linked immunoassay. Affinity purified, class-specific goat anti-human immunoglobulin specific for human IgG or IgM was obtained from Zymed (South San Francisco, CA). Each antibody was adsorbed on wells of a flexible flat-bottom microtiter tray (Dynatech Laboratory, Alexandria, VA) overnight at 4° C. After aspiration, each well was incubated in 1% bovine serum albumin (BSA) in phosphate-buffered saline (PBS) for an hour at room temperature. After washing 3 times with cold PBS/0.05% Tween-10, 10 μl hybridoma or trioma supernatant or, as a control, a known amount of purified human IgG or IgM was added, and the trays incubated for 1 hr at room temperature.

After washing 3 times with cold PBS/0.05% Tween-20 and air drying, 50 μL of dilute alkaline phosphatase conjugated goat anti-IgG or IgM heavy-chain specific antibody (Zymed) was added to each well (1:1000 dilution) and the plates incubated for 1 hr at room temperature. The plates were washed and 100 μl of p-nitrophenyl disodium phosphate (1 mg/ml) in 10% diethylamine buffer, pH 9.6, was added to each well. The plates were incubated ½ hr at room temperature in the dark. Color changes were read by Flow Titertek Multiskan MC Reader. The tests were specific for each immunoglobulin class over a range of 1 ng/ml to 50 nm/ml. Culture supernatants containing IgM and IgG antibodies were identified.

EXAMPLE IV

Anti-NANB Mab Production by Primate Trioma

The production of primate Mabs specific against NANB-infected liver was examined in several fused cell lines showing IgM production, as determined in Example III. In a first experiment, B-lymphocytes from NANB-infected chimpanzees were transformed with EBV, as in Example II, and cultures from five successful transformants were selected. Each of the five cultures was fused with hybridoma cell line SBC-H20, as in Example III, and colonies (two colonies for cultures 1–4 and one colony for culture 5) which showed IgM production were selected, and the colonies in each group pooled. The pooled cells in each trioma cell line gave the following staining patterns: cell line 1, nuclear; line 2, many cytoplasmic granules; line 3, granules near blood vessels; line 4, few cytoplasmic granules; and line 5, large globules and small granules.

The supernatants from each cell line were assayed for NANB-specific antibodies by the indirect immunofluorescence method of Example III, using sections of NANB-infected liver tissue. Each of the five lines gave a positive reaction. Cell line 2 was further tested for reactivity toward sections of liver infected with either hepatitis A or B virus. The IgM antibody produced by this line showed no binding to either of the two types of liver sections, indicating specificity toward NANB-infected liver tissue.

In a second study, non-transformed B-lymphocytes from NANB-infected chimpanzees were fused with hybridoma cell line SBC-H20, as in Example II, and the cells of either one or two fusions were pooled to give five separate fused cell lines. Each line was then screened for IgM production and between one and four colonies obtained for each line. The colonies from each line were pooled and stained as above, giving the following staining patterns: cell line 1, many medium granules; line 2, perinuclear; line 3, occasional small granules; line 4, clusters of small granules; and line 5, globules and rare granules.

Mabs produced by each cell line were reactive with liver slices from NANB-infected chimpanzees. Mabs produced by cell line 1 were also tested with liver from HAB and HBV infected chimpanzees. The antibodies showed no reactivity toward either liver tissue type, indicating specificity against antigens associated with NANB infection. This particular chimpanzee trioma produced by fusing EBV-transformed lymphocytes with SBC-H20 has been cultured over a fourl-month period, by repeated passage, and periodically examined for continued IgM production. It has showed continued IgM production after four months.

While exemplary embodiments and uses have been described herein, it will be appreciated that the invention encompasses a broad range of non-human primate Mabs and triomas for their production.

It is claimed:

1. A stable trioma cell line which secretes a chimpanzee IgM monoclonal antibody specific against an antigen associated with hepatitis nonA/nonB infection.

2. The cell line of claim 1, which has the characteristics of the cell line identified by ATCC deposit no. HB 8884.

3. A method of producing a chimpanzee IgM monoclonal antibody specific against an antigen associated with hepatitis nonA/nonB infection, comprising
   obtaining B lyphocytes from a chimpanzee infected with nonA/nonB hepatitis agent,
   transforming the B lymphocytes in vitro with Epstein-Barr virus,
   selecting transformed B lymphocytes which secrete antibodies specific against an antigen associated with hepatitis nonA/nonB infection,
   immortalizing the selected lymphocytes by fusion with a stable, non-antibody-secreting murine myeloma/human hybridoma cell line characterized by HLA surface antigens, to form stable antibody-secreting trioma cells, and
   selecting trioma cells which secrete antibody specific against the antigen.

4. The method of claim 3, wherein the trioma cells have the characteristics of ATTC No. HB 8884.

5. A chimpanzee IgM monoclonal antibody which is specific against an antigen associated with hepatitis nonA/nonB infection.

6. The chimpanzee monoclonal antibody produced by the trioma cell line characterized by ATCC No. HB 8884.

7. A chimpanzee IgM monoclonal antibody which is specific against an antigen associated with heptatitis nonA/nonB infection, which is derivatized with a fluorophore, chromophore, enzyme, or radiolabel.

8. A chimpanzee IgM monoclonal antibody which is specific against an antigen associated with hepatitis nonA/nonB infection which is attached to the surface of a solid support.

9. A chimpanzee IgM monoclonal antibody which is specific against an antigen associated with hepatitis nonA/nonB infection which is covalently attached to the surface of an affinity-chromatography support.

* * * * *